(12) United States Patent
Das et al.

(10) Patent No.: US 12,741,453 B2
(45) Date of Patent: Sep. 22, 2026

(54) CONSUMER PRODUCT

(71) Applicant: Conopco, Inc., Englewood Clliffs, NJ (US)

(72) Inventors: Sandip Das, Mumbai (IN); Daniella Wichuda Dario De-Leon, Quezon City (PH); James John Franklin, Stone (GB); Manoj Satish Ghatge, Satara (IN); Vo-Kien Trung, Ho Chi Minh City (VN); Elizabeth Jane Williams, Birkenhead (GB)

(73) Assignee: Conopco, Inc., Englewood Clliffs, NJ (US)

( * ) Notice: Subject to any disclaimer, the term of this patent is extended or adjusted under 35 U.S.C. 154(b) by 90 days.

(21) Appl. No.: 18/275,544

(22) PCT Filed: Feb. 16, 2022

(86) PCT No.: PCT/EP2022/053827

§ 371 (c)(1),
(2) Date: Aug. 2, 2023

(87) PCT Pub. No.: WO2022/175331

PCT Pub. Date: Aug. 25, 2022

(65) Prior Publication Data

US 2024/0123714 A1 Apr. 18, 2024

(30) Foreign Application Priority Data

Feb. 18, 2021 (IN) ............................ 202121006887
May 20, 2021 (EP) .................................... 21175068

(51) Int. Cl.
*B32B 27/08* (2006.01)
*A45D 40/00* (2006.01)
(Continued)

(52) U.S. Cl.
CPC .......... *B32B 27/08* (2013.01); *A45D 40/0087* (2013.01); *A61K 8/96* (2013.01);
(Continued)

(58) Field of Classification Search
CPC ..... B32B 27/08; B32B 27/32; A45D 40/0087; A61K 8/96; A61K 2800/87; A61Q 5/12
(Continued)

(56) References Cited

U.S. PATENT DOCUMENTS 4,706,802 A * 11/1987 Leigh .................. C11D 17/047 206/0.5
4,775,523 A 10/1988 Sparacio et al.
(Continued)

FOREIGN PATENT DOCUMENTS

DE 3727761 3/1998
EP 0925912 6/1999
(Continued)

OTHER PUBLICATIONS

Search Report and Written Opinion in EP21175068; Oct. 18, 2021; European Patent Office (EPO).
(Continued)

*Primary Examiner* — Rafael A Ortiz
(74) *Attorney, Agent, or Firm* — Carter, DeLuca & Farrell, LLP; George Likourezos; Bret P. Shapiro

(57) ABSTRACT

The present invention relates to a consumer product comprising a laminate packaging comprising an outer oriented multilayer film comprising a polyolefin-based polymer; an inner multilayer film comprising a polyolefin-based polymer; and a composition comprising 0.2% to 1.2% by weight of a perfume; wherein the outer and the inner layers are made of the same polyolefin-based polymer, which is eth-
(Continued)

100
105
110
120
130 ylene based polymer or propylene based polymer; and wherein the composition is packaged inside the laminate packaging.

13 Claims, 1 Drawing Sheet

(51) Int. Cl.

| | |
|---|---|
| ***A61K 8/96*** | (2006.01) |
| ***A61Q 5/12*** | (2006.01) |
| ***B32B 27/32*** | (2006.01) |
| ***B65B 3/04*** | (2006.01) |

(52) U.S. Cl.

CPC ................ *A61Q 5/12* (2013.01); *B32B 27/32* (2013.01); *B65B 3/04* (2013.01); *A61K 2800/87* (2013.01); *B32B 2250/242* (2013.01); *B32B 2255/10* (2013.01); *B32B 2255/205* (2013.01); *B32B 2307/516* (2013.01); *B32B 2307/518* (2013.01); *B32B 2307/724* (2013.01); *B32B 2307/7376* (2023.05); *B32B 2439/46* (2013.01)

(58) Field of Classification Search

USPC ........................................................ 206/484.1

See application file for complete search history.

(56) References Cited

U.S. PATENT DOCUMENTS

| | | | | |
|---|---|---|---|---|
| 5,518,790 | A * | 5/1996 | Huber ....................... | B32B 7/06 239/57 |
| 2007/0014993 | A1* | 1/2007 | Longmoore .......... | B32B 37/203 428/521 |
| 2010/0323134 | A1 | 12/2010 | Bostian et al. | |
| 2012/0033901 | A1 | 2/2012 | Votaw | |
| 2018/0339498 | A1 | 11/2018 | Zborowski et al. | |
| 2020/0317688 | A1* | 10/2020 | Haetzelt ................. | C11D 3/507 |

FOREIGN PATENT DOCUMENTS

| | | |
|---|---|---|
| KR | 20120041187 | 4/2012 |
| WO | WO2008074493 | 6/2008 |
| WO | WO2016135213 | 9/2016 |
| WO | WO2017087809 | 5/2017 |
| WO | WO2017102704 | 6/2017 |
| WO | WO2017120340 | 7/2017 |
| WO | WO2017127808 | 7/2017 |
| WO | WO2017184633 | 10/2017 |
| WO | WO2018000411 | 1/2018 |
| WO | WO2018045559 | 3/2018 |
| WO | WO2019108326 | 6/2019 |
| WO | WO2019132954 | 7/2019 |
| WO | WO2019156733 | 8/2019 |
| WO | WO2020120502 | 6/2020 |
| WO | WO2020133156 | 7/2020 |
| WO | WO2020133157 | 7/2020 |
| WO | WO2020136674 | 7/2020 |

OTHER PUBLICATIONS

Search Report and Written Opinion in PCTEP2022053827; May 30, 2022; World Intellectual Property Org. (WIPO).

Written Opinion of the International Preliminary Examionation Authority in PCTEP2022053827; Feb. 13, 2023; World Intellectual Property Org. (WIPO).

International Preliminary Report on Patentability in PCTEP2022053827; Apr. 26, 2023; World Intellectual Property Org. (WIPO).

* cited by examiner

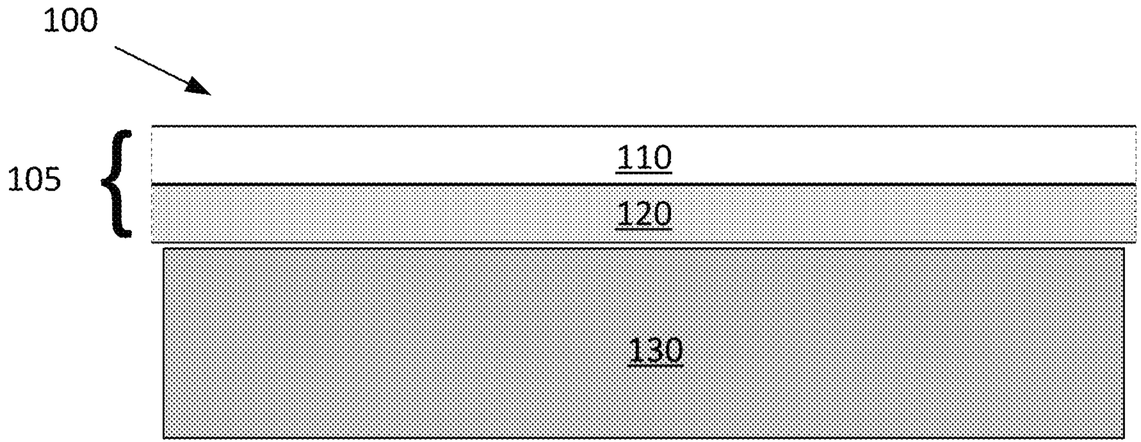
100
105
110
120
130

CONSUMER PRODUCT

CROSS-REFERENCE TO RELATED APPLICATIONS

This application is a U.S. national phase application under 35 U.S.C. § 371 of International Application No. PCT/EP2022/053827, filed on Feb. 16, 2022, which claims priority to Indian Patent Application number 202121006887, filed on Feb. 18, 2021, and European Patent Application No. 21175068.2, filed May 20, 2021, the entire disclosures of which are incorporated herein by reference in their entireties, for any and all purposes.

FIELD OF THE INVENTION

The present invention relates to a consumer product provided in a laminate packaging, in particular it relates to a consumer product provided in a flexible laminate packaging.

BACKGROUND OF THE INVENTION

Fragrances are perceived as an essential part of life.

In Personal Care and Home Care markets, most products rely upon fragrances to deliver valued emotional or functional benefits, to communicate product performance, to differentiate brands, or to create added value. On a functional level, the complex properties of fragrances allow individuals to control or remove malodour: the bad smells that afflict the everyday lives of millions. Control of these smells, using fragrances embedded in home and personal care products, improves the physical quality of people's lives, as well as combating malodour, fragrances communicate complex ideas—creating mood, signalling cleanliness, freshness, or softness, alleviating stress, creating well-being, and triggering allure and attraction.

It is habitual for consumers to open the cap of a bottle of a home or personal care product and smell the product, before buying the product when sold in a bottle. However, this is not possible when these products are sold in laminate packaging or sachets.

It is therefore an object of the present invention to provide a fragrance experience to consumers before the sale or use of the product when sold in laminate packaging or sachets without opening it.

It is another object of the present invention to provide a fragrance experience to consumer without affecting the shelf life of the product.

It is yet another object of the present invention to provide a fragrance experience to consumers before the sale or use of the product provided in a recyclable laminate packaging or sachet.

Surprisingly, it has been found that a fragrance experience of the product can be provided to the consumer before its sale or use by using perfume in a specific concentration in a composition packaged using a specific type of laminate.

SUMMARY OF THE INVENTION

Accordingly, in a first aspect, the present invention provides a consumer product comprising a laminate packaging comprising an outer oriented multilayer film comprising a polyolefin-based polymer; an inner multilayer film comprising a polyolefin-based polymer; and a composition comprising 0.2% to 1.2% by weight of a perfume; wherein the outer and the inner layers are made of the same polyolefin-based polymer, which is ethylene based polymer or propylene based polymer; and wherein the composition is packaged inside the laminate packaging.

In a second aspect, the present invention provides use of a laminate comprising an outer oriented multilayer film comprising a polyolefin-based polymer and an inner multilayer film comprising a polyolefin-based polymer for packaging home and personal care products to provide consumers with a fragrance experience before sale or use of the product.

In the context of the present invention, the reference to 'HDPE' means high-density polyethylene.

In the context of the present invention, the reference to 'LDPE' means low density polyethylene.

In the context of the present invention, the reference to 'MDPE' means medium density polyethylene.

In the context of the present invention, the reference to 'LLDPE' means linear low-density polyethylene.

In the context of the present invention, the reference to 'substantially free' typically means less than 3 wt %, preferably less than 2 wt %, more preferably less than 1 wt %, even more preferably 0 wt %.

In the context of the present invention, the reference to 'packaging' typically means non-rigid containers familiar to the skilled person. These may include sachets, pouches, stand-up pouches, pillow pouches, or bulk bags hulk bags, pre-made packages or the like.

In the context of the present invention, the reference to 'fragrance experience' means to be able to sense a particular fragrance or aroma.

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

BRIEF DESCRIPTION OF THE FIGURES

The foregoing and other features of this disclosure will become more fully apparent from the following description and appended claims, taken in conjunction with the accompanying drawing. Understanding that this drawing depicts only one embodiment in accordance with the disclosure and is, therefore, not to be considered limiting of its scope, the disclosure will be described with additional specificity and detail through use of the accompanying drawing, in which:

FIG. 1 illustrates a consumer product which includes laminated packaging including an outer oriented multilayered film, an inner multilayer film, and a composition, in accordance with the present disclosure.

DETAILED DESCRIPTION OF THE INVENTION

In a first aspect, the present invention relates to a consumer product comprising a laminate packaging and a perfumed composition.

The laminate packaging of the present invention is preferably a flexible laminate which is preferably recyclable.

The laminate packaging comprises an outer and an inner multilayer film comprising a polyolefin-based polymer.

The outer multilayer film is an oriented multilayer film. The outer film may be uniaxially oriented (machine direction) (MDO) or biaxially oriented (BO) multilayer film. Preferably, the outer multilayer film is a uniaxially oriented (machine direction) multilayer film.

The polyolefin-based polymer of the outer film is either an ethylene-based polymer (PE) or a propylene-based polymer (PP). Preferably, the polyolefin-based polymer is an ethylene-based polymer.

The outer oriented multilayer film of the present invention may comprise a plurality of layers comprising polyolefin-based polymer, preferably at least two, more preferably at least three, still more preferably at least four, even more preferably at least five, or even more than five layers. The layers are preferably composed of the same poly olefin-based polymer. A typical example of an outer oriented multilayer comprises several layers of different polyethylene (PE) resins such as HDPE, LDPE, MDPE, LLDPE.

The outer oriented multilayer film preferably has a thickness of 15 to 30 microns, more preferably 20 to 26 microns, still more preferably at least 21 microns, even more preferably at least 22 microns, or even at least 23 microns, but typically not more than microns, preferably not more than 24 microns.

The outer oriented multilayer film preferably has a density of 0.90 to 0.98 g/cm 3 (kg/l), more preferably 0.93 to 0.95 g/cm 3 (kg/l).

Commercial examples of the outer oriented multilayer film of the present invention include LamiBel® (ex PlasBel®). They are also available in the market from various suppliers such as Alliance Packing Plastic JSC (APLAS) (Vietnam), Thanh Phu Plastic Packaging Co., Ltd (Vietnam), Constantia Creative Polypack Limited (India), RKW (Sweden), Polysack Flexible Packaging (Israel) and Coveris (Austria).

The inner multilayer film comprising a polyolefin-based polymer may also be called a sealant film or a blown sealant film. Unlike the oriented multilayer film, the inner multilayer film is not oriented.

This inner film is preferably vacuum metallized which is thought to provide combined properties of a barrier and a sealant. After the polyolefin film is blown, the film is metallized using aluminium vapour of 99.9% purity under vacuum condition, which enhances the moisture and oxygen barrier of the film.

The polyolefin-based polymer of the inner multilayer film is either an ethylene-based polymer (PE) or and propylene-based polymer (PP). Preferably, the polyolefin-based polymer is an ethylene-based polymer.

The inner multilayer film of the present invention may comprise a plurality of layers comprising polyolefin-based polymer, preferably at least two, more preferably at least three, still more preferably at least four, even more preferably at least five, or even more than five layers. The layers are preferably composed of the same polyolefin-based polymer. A typical example of an inner multilayer comprises several layers of different polyethylene (PE) resins such as HDPE, LDPE, MDPE and LLDPE.

The inner multilayer of the present invention preferably has a thickness of 30 to 60 microns. The inner multilayer more preferably has a thickness of 30 to 50 microns or even 35 to 45 microns, still more preferably at least 37 microns, even more preferably at least 38 microns, or even at least 39 microns, but typically not more than 43 microns, preferably not more than 41 microns, more preferably not more than 40 microns. By micron is meant micrometer.

The inner multilayer film preferably has a density of 0.90 to 0.96 g/cm$^3$ (kg/l), more preferably 0.93 to 0.94 g/cm$^3$ (kg/l).

Commercial examples of the outer oriented multilayer film of the present invention include CEL-MET™ Sealant film. They are also available in the market from various suppliers such as Alliance Packing Plastic JSC (APLAS) (Vietnam), Huhtamaki (India), Amcor (Thailand), DNP Indonesia, Plasindo (Indonesia).

To be able to provide a recyclable laminate packaging, the outer and the inner films are made of the same polyolefin-based polymer, which is ethylene based polymer or propylene based polymer. When the laminate is made of either one of the polymer, it is substantially free of the other polymer.

In a preferred embodiment, the outer oriented multilayer film comprises a polymer consisting of a polyolefin-based polymer; and the inner multilayer film comprises a polymer consisting of a polyolefin-based polymer; and the outer and the inner films are made of the same polyolefin-based polymer, which is ethylene based polymer or propylene based polymer. When the laminate is made of either one of the polymer, it is substantially free of the other polymer.

Additionally, the laminate may comprise an adhesive layer. The adhesive layer is preferably disposed between the outer and the inner multilayer films.

Various adhesive compositions are considered suitable for the adhesives used in the laminate. These may include polyurethane, epoxy, acrylic, or the like. Preferably, the laminate comprises adhesive layer comprising polyurethane adhesive. The polyurethane adhesive may be solventless, waterborne or solvent based. Furthermore, the polyurethane adhesive may be a two-part formulation.

Alternatively, the outer and the inner multilayer films may be heat sealed instead of applying an adhesive composition.

The weight or thickness of the adhesive layer can depend on a number of factors including, for example, the desired thickness of the laminate, the type of adhesive used, and other factors. Preferably, the adhesive layer is applied at up to 4 g/m$^2$, more preferably from 1 to 3 g/m$^2$, even more preferably from 1.5 to 2.5 g/m$^2$, most preferably 2 g/m$^2$.

The laminate packaging of the present invention has an oxygen transmission rate (OTR) of 2 to 20, preferably at least 3, more preferably at least 4 but typically not more than 15, preferably not more than 10, more preferably not more than 8, even more preferably not more than 6 or even 5 cm$^3$/m$^2$/day at 23° C., 0% RH. A commonly used unit of OTR is the cm$^3$ (STP)/(PKG·d), where 1 cm$^3$ at Standard Temperature and Pressure (STP=273.15K; $1.013\times10^5$ Pa) is $44.62\times10^{-6}$ mol and one day is 86 400 s. Oxygen transmission rate (OTR) as applied to a package, is the quantity of oxygen gas passing through the surface of the package (PKG) per unit of time It may be measured using ASTM D3985: The specimen of 50 cm$^2$ is mounted as a sealed semi-barrier between two chambers at ambient atmospheric pressure of 1013 mbar.

Temperature and humidity inside the chamber are critical parameters influencing final test data which are maintained at 23° C. at 0% RH respectively, in this case. One chamber is slowly purged by a stream of 100% nitrogen and the other chamber contains 100% oxygen. As oxygen gas permeates through the film into the nitrogen carrier gas, it is transported to the coulometric detector where it produces an electrical current, the magnitude of which is proportional to the amount of oxygen ($cm^3$) flowing into the detector per unit time (day) for the given area ($m^2$) for the particular sample. Among that, oxygen gas is the testing gas and nitrogen gas is the carrier gas. Oxygen gas concentration of upper chamber is higher than that of lower chamber, due to which certain concentration difference is formed between both sides of specimen. During the transmission process, oxygen gas transmits from upper chamber through specimen into lower chamber. Final results are reported as rate of oxygen transmission ($cm^3$) measured per unit area ($m^2$) per unit time (day) i.e. $cm^3/m^2$/day. And wherein samples are measured after a fixed period of time, preferably 1 day, or 2 days, or one week, or two weeks, or one month.

The consumer product of the present invention comprises a composition comprising 0.2% to 1.2%, preferably at least 0.3%, more preferably at least 0.4%, even more preferably at least 0.5% but typically not more than 1%, preferably not more than 0.8%, even more preferably not more than 0.6% by weight of a perfume.

It is critical to maintain the concentration of perfume in the composition to less than 1.2% by weight to keep optimum concentration of fragrance molecule inside the home or personal care formulation (e.g. a shampoo formulation) so that it does not migrate faster.

Perfumes may be defined as a preparation that releases a pleasant smell and that is usually a liquid based on natural or synthetic ingredients.

The perfume used in the composition of the present invention is typically used as a functional fragrance to enhance another product like home or personal care products such as shampoos, detergents etc.

The term "fragrance raw material" in the context of this invention typically denotes a material which is used essentially for its ability to impart a pleasant odour to a composition (into which it is incorporated), and/or a surface (to which it is applied), either on its own or in admixture with other such materials. Materials having these characteristics are generally small, lipophilic molecules of sufficient volatility to be transported to the olfactory system in the upper part of the nose.

"Fragrance raw materials" may encompass any suitable materials for fragrance uses, including materials such as, for example, alcohols, aldehydes, ketones, esters, ethers, acetates, nitriles, terpene hydrocarbons, nitrogenous or sulfurous heterocyclic compounds and essential oils. However, naturally occurring plant and animal oils and exudates comprising complex mixtures of various chemical components are also known for use as "fragrance raw materials". The individual perfume raw materials which comprise a known natural oil may be found by reference to Journals commonly used by those skilled in the art such as "Perfume and Flavourist" or "Journal of Essential Oil Research", or listed in reference texts such as the book by S. Arctander, Perfume and Flavor Chemicals, 1969, Montclair, N.J., USA and more recently re-published by Allured Publishing Corporation Illinois (1994). Additionally, some perfume raw materials are supplied by the fragrance houses (Firmenich, International Flavors & Fragrances, Givaudan, Symrise) as mixtures in the form of proprietary speciality accords.

A wide variety of chemicals are known for fragrance (i.e., perfume) uses. The perfume herein may be relatively simple in their compositions, comprising a single chemical, or can comprise highly sophisticated complex mixtures of natural and synthetic chemical components, all chosen to provide any desired odor.

Fragrance raw materials for use in the invention will typically have molecular weights of less than 325 atomic mass units, preferably less than 300 atomic mass units and more preferably less than 275 atomic mass units. The molecular weight is preferably greater than 100 atomic mass units and more preferably greater than 125 atomic mass units, since lower masses may be too volatile and/or insufficiently lipophilic to be effective.

Fragrance raw materials for use in the invention will preferably have a molecular structure which does not contain halogen atoms and/or strongly ionizing functional groups such as sulfonates, sulfates, or quaternary ammonium ions.

Fragrance raw materials for use in the invention will more preferably have a molecular structure containing only atoms from among, but not necessarily all, of the following: hydrogen, carbon, oxygen, nitrogen and sulphur. Most preferably the fragrance raw materials will have a molecular structure containing only atoms from among, but not necessarily all, of the following: hydrogen, carbon and oxygen.

Examples of fragrance raw materials for use in the invention include aromatic, aliphatic and araliphatic hydrocarbons having molecular weights from about 90 to about 250; aromatic, aliphatic and araliphatic esters having molecular weights from about 130 to about 250; aromatic, aliphatic and araliphatic nitriles having molecular weights from about 90 to about 250; aromatic, aliphatic and araliphatic alcohols having molecular weights from about 90 to about 240; aromatic, aliphatic and araliphatic ketones having molecular weights from about 150 to about 270; aromatic, aliphatic and araliphatic lactones having molecular weights from about 130 to about 290; aromatic, aliphatic and araliphatic aldehydes having molecular weights from about 90 to about 230; aromatic, aliphatic and araliphatic ethers having molecular weights from about 150 to about 270; and condensation products of aldehydes and amines having molecular weights from about 180 to about 320.

Specific examples of fragrance raw materials for use in the invention include:

i) hydrocarbons, such as, for example, D-limonene, 3-carene, a-pinene, b-pinene, a-terpinene, g-terpinene, p-cymene, bisabolene, camphene, caryophyllene, cedrene, farnesene, longifolene, myrcene, ocimene, valencene, (E,Z)-1,3,5-undecatriene, styrene, and diphenylmethane;

ii) aliphatic and araliphatic alcohols, such as, for example, benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, 1-(4-isopropylphenyl)ethanol, hexanol, octanol, 3-octanol, 2,6-dimethylheptanol, 2-methyl-2-heptanol, 2-methyl-2-octanol, (E)-2-hexenol, (E)- and (Z)-3-hexenol, 1-octen-3-ol, a mixture of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxyoctan-2-ol, 9-decenol, 10-undecenol, and 4-methyl-3-decen-5-ol;

iii) cyclic and cycloaliphatic alcohols, such as, for example, 4-tert-butylcyclohexanol, 3,3,5-trimethylcyclohexanol, 3-isocamphylcyclohexanol, 2,6,9-trimethyl-Z2,Z5,E9-cyclododecatrien-1-ol, 2-isobutyl-4-methyltetrahydro-2H-pyran-4-ol, alpha, 3,3-trimethylcyclo-hexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol, and 1-(2,2,6-trimethylcyclohexyl)hexan-3-ol;

iv) aliphatic aldehydes and their acetals, such as, for example, hexanal, heptanal, octanal, nonanal, decanal, undecanal, dodecanal, tridecanal, 2-methyloctanal, 2-methylnonanal, 2-methylundecanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal-diethylacetal, 1,1-dimethoxy-2,2,5-trimethyl-4-hexene, and citronellyl oxyacetaldehyde;

v) aliphatic ketones and oximes thereof, such as, for example, 2-heptanone, 2-octanone, 3-octanone, 2-nonanone, 5-methyl-3-heptanone, 5-methyl-3-heptanone oxime, and 2,4,4,7-tetramethyl-6-octen-3-one;

vi) aliphatic sulfur-containing compounds, such as, for example, 3-methylthiohexanol, 3-methylthiohexyl acetate, 3-mercaptohexanol, 3-mercaptohexyl acetate, 3-mercaptohexyl butyrate, 3-acetylthiohexyl acetate, and 1-menthene-8-thiol;

vii) aliphatic nitriles, such as, for example, 2-nonenenitrile, 2-tridecenenitrile, 2,12-tridecenenitrile, 3,7-dimethyl-2,6-octadienenitrile, and 3,7-dimethyl-6-octenenitrile;

viii) aliphatic carboxylic acids and esters thereof, such as, for example, (E)- and (Z)-3-hexenylformate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexylbutyrate, (E)- and (Z)-3-hexenyl isobutyrate, hexyl crotonate, ethylisovalerate, ethyl-2-methyl pentanoate, ethyl hexanoate, allyl hexanoate, ethyl heptanoate, allyl heptanoate, ethyl octanoate, ethyl-(E,Z)-2,4-decadienoate, methyl-2-octinate, methyl-2-noninate, allyl-2-isoamyl oxyacetate, and methyl-3,7-dimethyl-2,6-octadienoate;

ix) acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

x) acyclic terpene aldehydes and ketones, such as, for example, geranial, neral, citronellal, 7-hydroxy-3,7-dimethyloctanal, 7-methoxy-3,7-dimethyloctanal, 2,6,10-trimethyl-9-undecenal, osinensal, b-sinensal, geranylacetone, as well as the dimethyl- and diethylacetals of geranial, neral and 7-hydroxy-3,7-dimethyloctanal;

xi) cyclic terpene alcohols, such as, for example, menthol, isopulegol, alpha-terpineol, terpinen-4-ol, menthan-8-ol, menthan-1-ol, menthan-7-ol, borneol, isoborneol, linalool oxide, nopol, cedrol, ambrinol, vetiverol, guaiol, and the formates, acetates, propionates, isobutyrates, butyrates, isovalerates, pentanoates, hexanoates, crotonates, tiglinates and 3-methyl-2-butenoates of alpha-terpineol, terpinen-4-ol, methan-8-ol, methan-1-ol, methan-7-ol, borneol, isoborneol, linalool oxide, nopol, cedrol, ambrinol, vetiverol, and guaiol;

xii) cyclic terpene aldehydes and ketones, such as, for example, menthone, isomenthone, 8-mercaptomenthan-3-one, carvone, camphor, fenchone, a-ionone, b-ionone, a-n-methylionone, b-n-methylionone, a-isomethylionone, b-isomethylionone, alpha-irone, o damascone, b-damascone, b-damascenone, d-damascone, g-damascone, 1-(2,4,4-trimethyl-2-cyclohexen-1-yl)-2-buten-1-one, 1,3,4,6,7,8a-hexahydro-1,1,5,5-tetramethyl-2H-2,4a-methanonaphthalen-8(5H)-one, nootkatone, dihydronootkatone and cedryl methyl ketone;

xiii) cyclic and cycloaliphatic ethers, such as, for example, cineole, cedryl methyl ether, cyclododecyl methyl ether, (ethoxymethoxy)cyclododecane; alpha-cedrene epoxide, 3a,6,6,9a-tetramethyldodecahydronaphtho[2,1-b]furan, 3a-ethyl-6,6,9a-trimethyldodecahydronaphtho[2,1-b]furan, 1,5,9-trimethyl-13-oxabicyclo[10.1.0]-trideca-4,8-diene, rose oxide and 2-(2,4-dimethyl-3-cyclohexen-1-yl)-5-methyl-5-(1-methylpropyl)-1,3-dioxane;

xiv) cyclic ketones, such as, for example, 4-tert-butylcyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetramethylcyclohexanone, 4-tert-pentylcyclohexanone, 5-cyclohexadecen-1-one, 6,7-dihydro-1,1,2,3,3-pentamethyl-4(5H)-indanone, 5-cyclohexadecen-1-one, 8-cyclohexadecen-1-one, 9-cycloheptadecen-1-one and cyclopentadecanone;

xv) cycloaliphatic aldehydes and ketones, such as, for example, 2,4-dimethyl-3-cyclohexene carbaldehyde, 2-methyl-4-(2,2,6-trimethyl-cyclohexen-1-yl)-2-butenal, 4-(4-hydroxy-4-methylpentyl)-3-cyclohexene carbaldehyde, 4-(4-methyl-3-penten-1-yl)-3-cyclohexene carbaldehyde, 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphtalenyl methyl-ketone, methyl-2,6,10-tri methyl-2,5,9-cyclododecatrienyl ketone and tert-butyl-(2,4-dimethyl-3-cyclohexen-1-yl) ketone;

xvi) esters of cyclic alcohols, such as, for example, 2-tert-butylcyclohexyl acetate, 4-tert-butylcyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5 or 6-indenyl acetate, 4,7-methano-3a,4,5,6,7,7a-hexahydro-5 or 6-indenyl propionate, 4,7-methano-3a,4,5,6,7,7a-hexahydro-5 or 6-indenyl-isobutyrate and 4,7-methanooctahydro- or 6-indenyl acetate;

xvii) esters of cycloaliphatic carboxylic acids, such as, for example, allyl 3-cyclohexyl-propionate, allyl cyclohexyl oxyacetate, methyl dihydrojasmonate, methyl jasmonate, methyl 2-hexyl-3-oxocyclopentanecarboxylate, ethyl 2-ethyl-6,6-dimethyl-2-cyclohexenecarboxylate, ethyl 2,3,6,6-tetramethyl-2-cyclohexenecarboxylate and ethyl 2-methyl-1,3-dioxolane-2-acetate;

xviii) esters of araliphatic alcohols and aliphatic carboxylic acids, such as, for example, benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, a-trichloromethylbenzyl acetate, a,a-dimethylphenylethyl acetate, a,a-dimethylphenylethyl butyrate, cinnamyl acetate, 2-phenoxyethyl isobutyrate and 4-methoxybenzyl acetate;

xix) araliphatic ethers and their acetals, such as, for example, 2-phenylethyl methyl ether, 2-phenylethyl isoamyl ether, 2-phenyethyl cyclohexyl ether, 2-phenylethyl-1-ethoxyethyl ether, phenylacetaldehyde dimethyl acetal, phenylacetaldehyde diethyl acetal, 2-phenylpropionaldehyde dimethyl acetal, phenylacetaldehyde glycerol acetal, 2,4,6-trimethyl-4-phenyl-1,3-dioxane, 4,4a,5,9b-tetrahydroindeno[1,2-d]-m-dioxin and 4,4a,5,9b-tetrahydro-2,4-dimethylindeno[1,2-d]-m-dioxin;

xx) aromatic and araliphatic aldehydes and ketones, such as, for example, benzaldehyde; phenylacetaldehyde, 3-phenylpropanal, 2-phenyl propanal, 4-methylbenzaldehyde, 4-methylphenylacetaldehyde, 3-(4-ethylphenyl)-2,2-dimethylpropanal, 2-methyl-3-(4-isopropylphenyl)propanal, 2-methyl-3-(4-tert-butylphenyl) propanal, 3-(4-tert-butylphenyl)propanal, cinnamaldehyde, alpha-butylcinnamaldehyde, alpha-amylcinnamaldehyde, alpha-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylene-dioxybenzaldehyde, 3,4-dimethoxybenzaldehyde, 2-methyl-3-(4-methoxyphenyl)propanal, 2-methyl-3-(4-methylendioxyphenyl)propanal, acetophenone, 4-methylacetophenone, 4-methoxyacetophenone, 4-tert-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert.-butyl-1,1-dimethyl-4-indanyl methyl ketone, 1-[2,3-dihydro-1,1,2,6-tetramethyl-3-(1-methyl-ethyl)-1H-5-indenyl] ethanone and 5',6',7',8'-tetrahydro-3',5',5',6',8',8'-hexamethyl-2-acetonaphthone;

xxi) aromatic and araliphatic carboxylic acids and esters thereof, such as, for example, benzoic acid, phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate and ethyl 3-methyl-3-phenylglycidate;

xxii) nitrogen-containing aromatic compounds, such as, for example, 2,4,6-trinitro-1,3-dimethyl-5-tert-butylbenzene, 3,5-dinitro-2,6-dimethyl-4-tert-butylacetophenone, cinnamonitrile, 5-phenyl-3-methyl-2-pentenonitrile, 5-phenyl-3-methylpentanonitrile, methyl anthranilate, methyl-N-methylanthranilate, Schiff's bases of methyl anthranilate with 7-hydroxy-3,7-dimethyloctanal, 2-methyl-3-(4-tert.-butylphenyl)propanal or 2,4-dimethyl-3-cyclohexene carbaldehyde, 6-isopropylquinoline, 6-isobutylquinoline, 6-sec-butylquinoline, indole, skatole, 2-methoxy-3-isopropylpyrazine and 2-isobutyl-3-methoxypyrazine;

xxiii) phenols, phenyl ethers and phenyl esters, such as, for example, estragole, anethole, eugenol, eugenyl methyl ether, isoeugenol, isoeugenol methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl) phenol and p-cresyl phenylacetate;

xxiv) heterocyclic compounds, such as, for example, 2,5-dimethyl-4-hydroxy-2H-furan-3-one, 2-ethyl-4-hydroxy-5-methyl-2H-furan-3-one, 3-hydroxy-2-methyl-4H-pyran-4-one, 2-ethyl-3-hydroxy-4H-pyran-4-one;

xxv) lactones, such as, for example, 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis- and trans-1'-pentadecen-1,15-olide, cis- and trans-12-pentadecen-1,15-olide, 1,16-hexadecanolide, 9-hexadecen-1,16-olide, 10-oxa-1,16-hexadecanolide, 11-oxa-1,16-hexadecanolide, 12-oxa-1,16-hexadecanolide, ethylene-1,12-dodecanedioate, ethylene-1,13-tridecanedioate, coumarin, 2,3-dihydrocoumarin, and octahydrocoumarin.

Naturally occurring exudates such as essential oils extracted from plants may also be used as fragrance raw materials in the invention. Essential oils are usually extracted by processes of steam distillation, solid-phase extraction, cold pressing, solvent extraction, supercritical fluid extraction, hydrodistillation or simultaneous distillation-extraction.

Essential oils may be derived from several different parts of the plant, including for example leaves, flowers, roots, buds, twigs, rhizomes, heartwood, bark, resin, seeds and fruits. The major plant families from which essential oils are extracted include Asteraceae, Myrtaceae, Lauraceae, Lamiaceae, Myrtaceae, Rutaceae and Zingiberaceae. The oil is "essential" in the sense that it carries a distinctive scent, or essence, of the plant.

Essential oils are understood by those skilled in the art to be complex mixtures which generally consist of several tens or hundreds of constituents. Most of these constituents possess an isoprenoid skeleton with 10 atoms of carbon (monoterpenes), atoms of carbon (sesquiterpenes) or 20 atoms of carbon (diterpenes). Lesser quantities of other constituents can also be found, such as alcohols, aldehydes, esters and phenols.

However, an individual essential oil is usually considered as a single ingredient in the context of practical fragrance formulation. Therefore, an individual essential oil may be considered as a single fragrance raw material for the purposes of this invention.

Specific examples of essential oils for use as fragrance raw material in the invention include cedarwood oil, juniper oil, cumin oil, cinnamon bark oil, camphor oil, rosewood oil, ginger oil, basil oil, eucalyptus oil, lemongrass oil, peppermint oil, rosemary oil, spearmint oil, tea tree oil, frankincense oil, chamomile oil, clove oil, jasmine oil, lavender oil, rose oil, ylang-ylang oil, bergamot oil, grapefruit oil, lemon oil, lime oil, orange oil, fir needle oil, galbanum oil, geranium oil, grapefruit oil, pine needle oil, caraway oil, labdanum oil, lovage oil, marjoram oil, mandarin oil, clary sage oil, nutmeg oil, myrtle oil, clove oil, neroli oil, patchouli oil, sandalwood oil, thyme oil, verbena oil, vetiver oil and wintergreen oil.

The number of different fragrance raw materials contained in the perfume may be at least 4, preferably at least 6, more preferably at least 8 and most preferably at least 10, such as from 10 to 200 and more preferably from 10 to 100.

The perfume of the present invention is a composition typically comprising 90% to 100% by weight of fragrance raw materials, preferably 92% to 100%, more preferably 95% to 100%, still more preferably 98% to 100%, even more preferably 100%.

Raw materials may either be natural, synthetic or a mixture of both. When the raw materials are a mixture of natural and synthetic, not more than 5% by weight of the raw materials make up the natural raw materials, preferably not more than 4%, more preferably not more than 3%, even more preferably not more than 2% by weight of the raw materials.

The perfume of the present invention may optionally comprise a solvent, in particular alcoholic solvents, such as linear or branched alcoholic solvents, having 1 to 4 carbon atoms and at least one hydroxyl functional group. Said solvents include, ethanol, 1-propanol, 2-propanol, 1-butanol, 1,2-butanediol, 1,2-pentandiol 1,2-hexanediol, 1,2-heptanediol, 2-methyl-pentan-2,4-diol; glycol ethers, such as propylene glycol, dipropylene glycol, 1,3-propanediol Dowanol™ DPM, Dowanol™ TPM, Dowanol™ DPnP; methyl methoxy butanol, and mixture thereof.

When present, the solvent is present in the perfume at a concentration of up to 10% by weight.

In a preferred embodiment, the perfume is substantially free of a solvent. As used hereinabove, the term “substantially free” means less than 5% by weight of perfume, preferably less than 3%, more preferably less than 2%, most preferably 0%.

In a preferred embodiment, the perfume of the present invention consists of 90% to 100% by weight of perfume raw materials, preferably 95 to 100%, more preferably 98% to 100%, most preferably 100%; and 0% to 10% by weight of solvents, preferably 0% to 5%, more preferably 0% to 2%, most preferably 0%.

Without wishing to be bound by theory, it is believed that by maintaining the concentration of perfume between 0.2% to 1.2% only a slow migration of fragrance through the laminate packaging according to the invention is allowed in order to extend the time for the fragrance to reach its steady state. The consumer can smell the perfume without opening the sachet but at the same time, due to the slow migration rate, the shelf life is not affected.

The composition of the present invention is preferably an aqueous based composition. As shown in FIG. 1, consumer product 100 includes laminated packaging 105 (including an outer oriented multilayered film 110 and an inner multilayer film 120) and a composition 130 comprising 0.2% to 1.2% by weight perfume. Preferably, the composition is a domestic cleaning liquid. Preferred examples of such liquids include personal cleaning liquids such as soaps, shampoos and hair/skin conditioners. Other examples of such liquids include laundry (washing and/or conditioning), manual or automatic dishwashing (washing and/or rinse aids) and hard surface cleaning fluids.

In a second aspect, the present invention relates to the use of a laminate comprising an outer oriented multilayer film comprising a polyolefin-based polymer and an inner multilayer film comprising a polyolefin-based polymer for packaging home and personal care products to provide consumers with a fragrance experience before sale or use of the product.

The invention will now be further described by reference to the following non-limiting examples. In the examples, all percentages are by weight based on total weight, unless otherwise specified.

EXAMPLES

Example 1: Odour Assessments of Haircare Products Stored in Sachet Packaging In this example a conditioner composition stored in the laminate packaging according to the invention (Ex1) was compared with the composition stored in various other laminates (Control, B1, B1+) on shelf life of the composition. The conditioner composition used in this example is provided in table 1 and the laminates in table 2.

TABLE 1

| Conditioner composition | |
|---|---|
| Ingredients | Parts by wt |
| Water | 87.2 |
| Cetearyl Alcohol | 5 |
| STEARAMIDOPROPYL DIMETHYLAMINE | 0.4 |
| Behentrimonium Chloride | 1.6 |
| Lactic Acid 90% | 0.1 |
| Disodium EDTA | 0.1 |
| Dimethicone 600K and Amodimethicone | 4.3 |
| CI 17200 Acid Red 33 | 0.2 |
| L-lysine monohydrochloride | 0.02 |
| Perfume (100% active) | 1 |
| D,L-Panthenol 50% | 0.01 |
| Hydrolysed Keratin 20% | 0.001 |
| Methylparaben | 0.2 |
| CIT:MIT | 0.06 |

TABLE 2

| Laminates | |
|---|---|
| Example | Laminate layers |
| Control | 10PET/10MPET/30LDPE |
| B1 | 18BOPP/18VMBOPP/30PE |
| B1+ | 18BOPP/18VMBOPP/40PE |
| Ex 1 | 23MDOPE/40VMPE |

the number indicates thickness in micrometer
BO: biaxially oriented
VM: vacuum metalized
MDO: machine direction oriented Procedure for Odour Assessment:

Strips of each sample set were taken—each containing 12 individual sachets. They were all visually inspected and conditioned for 24 hours prior to testing in room temperature (18-25° C.). Any sachet strip that showed any visual defects (e.g. leakage) were discarded.

Each sachet strip, including control sachets were individually labelled and then placed into storage ovens set at the conditions below—so that they were hanging vertically. This was done using foldback clips, clipping the top sachet to the racking in the storage ovens. All sachet strips were spaced out in the storage ovens so that separate strips were not in contact with each other.

Condition set 1—4° C.

Condition set 2—25° C.

Condition set 3—45° C.

Two individual sachets from each sample from each set of storage condition was removed from storage after 2 weeks, 4 weeks, 8 weeks and 12 weeks for fragrance analysis and left for at least 2 hours to equilibrate to room temperature.

Glass jars suitable for fragrance assessments were then labelled appropriately to correspond with each specific sachet sample, ready for the sample to be decanted from the sachet. The corresponding sachet to the labelled jar is cut open at one end using scissors and the contents were squeezed into the glass jar with the lid replaced onto the jar after. An equilibration period of at least one hour was observed to allow the product to settle and the headspace of the formulation to build.

The samples were assessed by user taking short, small sniffs and by providing an odour assessment score on a scale of 0-5 as shown in Table 3.

TABLE 3

| Score | Description | Odour Intensity/ Note Result |
|---|---|---|
| 0 | No change | PASS |
| 1 | Very slight/Just Detectable | PASS |
| 2 | Slight Change | PASS |
| 3 | Moderate/Clearly Detectable Change | BORDERLINE |
| 4 | Strong Change | FAIL |
| ≥5 | Extreme and Unacceptable Change | FAIL |

Test samples were compared back to the corresponding control at the same storage condition. For example, test sample at 4° C. was compared to control sample at 4° C. and test sample at 25° C. was compared to control sample at 25° C.

User scored any differences detected between test and control odours at each storage condition using the scale in table 3.

TABLE 4

| | Result | | | | | | | | | | | |
|---|---|---|---|---|---|---|---|---|---|---|---|---|
| | 2 weeks Temperature | | | 4 weeks Temperature | | | 8 weeks Temperature | | | 12 weeks Temperature | | |
| Sachet | 4° C. | 25° C. | 45° C. | 4° C. | 25° C. | 45° C. | 4° C. | 25° C. | 45° C. | 4° C. | 25° C. | 45° C. |
| Ctrl | 0 | 0 | 0 | 0 | 0 | 0 | 0 | 0 | 0 | 0 | 0 | 0 |
| B1 | 0 | 0 | 1 | 0 | 0 | 1 | 0 | 0 | 1 | 0 | 0 | 1 |
| B1+ | 0 | 0 | 1 | 0 | 0 | 1 | 0 | 0 | 1 | 0 | 0 | 1 |
| Ex 1 | 0 | 0 | 1 | 0 | 0 | 1 | 0 | 1 | 1 | 0 | 1 | 2 |

Results of the odour assessment indicate that from 8 weeks of storage at room temperature, there is a slight odour or change in fragrance of the composition according to the invention (Ex 1) stored in the sachet which is the result of the perfume molecules migrating through the laminate, however not at a fast rate that the shelf life of the product is affected.

Example 2: To Assess the Impact of the Sachet Laminate on the Overall Consumer Experience of the Fragrance of a Shampoo Enclosed in a Sachet Before Opening of the Sachet The test participants recruited fall within the following criteria of regular users of the product (market demographic of product variant).

Females, 18-30 years

LSM 5+, living in same city of test location

Current users of same product variant

Each participant was given two marked envelopes

Envelope marked A: 12 Sunsilk Strong & Long sachets in a link—current market sachet material—B1+

Envelope marked B: 12 Sunsilk Strong & Long sachets in a link—using the packaging laminate according to the invention Both products contained the exact same formulation and fragrance as controlled variables with only the laminate as the test variable to determine the impact of the sachet material on the overall fragrance experience of the test participants.

Participants were asked the following:

Participants were asked whether they can smell the fragrance from the outside of the sachet prior to opening it Result:

12 out of 12 confirmed that they can smell the fragrance from outside of product B (packaging laminate according to the invention) sachet prior to opening it, unlike product A or their regular products wherein they have NOT experienced this before.

This concludes that based on the participants experience the packaging laminate according to the invention allows for some fragrance to be able to pass through from the sachet to allow consumers to experience it from outside the sachet laminate without opening the sachet—while the current sachet material seals in the fragrance completely.

The invention claimed is:

1. A consumer product comprising:

a laminate packaging comprising an outer oriented multilayer film comprising a polyolefin-based polymer and an inner multilayer film comprising a polyolefin-based polymer; and a liquid composition comprising 0.2% to 1.2% by weight of a perfume;

wherein the outer and the inner layers are made of the same polyolefin-based polymer, which is an ethylene based polymer or propylene based polymer; and wherein the composition is packaged by the laminated packaging and stored inside the laminate packaging and the laminate packaging allows perfume in the composition stored inside the laminate packaging to pass through the laminate packaging to provide consumers with a fragrance experience before sale or use of the consumer product.

2. The consumer product according to claim 1 wherein the perfume comprises 90% to 100% by weight of fragrance raw materials.

3. The consumer product according to claim 1 wherein the outer multilayer has a thickness of 20 to 26 μm.

4. The consumer product according to claim 1 wherein the inner multilayer has a thickness of 30 to 60 μm.

5. The consumer product according to claim 1 wherein the oriented layer is uniaxially (machine direction) or biaxially oriented multilayer film.

6. The consumer product according to claim 1 wherein the oriented multilayer film is uniaxially (machine direction) oriented polyethylene film.

7. The consumer product according to claim 1 wherein the composition comprises 0.5% to 1% by weight of a perfume.

8. The consumer product according to claim 1 wherein the composition is a personal care or home care composition.

9. The consumer product according to claim 1 wherein the composition is an aqueous based composition.

10. The consumer product according to claim 1 wherein the inner multilayer film is vacuum metalized.

11. The consumer product according to claim 1 wherein the composition is a domestic cleaning liquid.

12. A method of making packaging for home and personal care products that provides consumers with a fragrance experience before sale or use of the products, comprising:

providing a laminate packaging comprising an outer oriented multilayer film comprising a polyolefin-based polymer, and an inner multilayer film comprising a polyolefin-based polymer;

providing a liquid composition comprising 0.2% to 1.2% by weight of a perfume; and packaging the composition by the laminated packaging so that the composition is stored inside the laminate packaging, wherein the laminate packaging allows perfume in the composition stored inside the laminate packaging to pass through the laminate packaging to provide consumers with a fragrance experience before sale or use of the consumer product.

13. The method according to claim 12 wherein the outer oriented multilayer film and the inner multilayer film are made of the same polyolefin-based polymer, which is ethylene based polymer or propylene based polymer.

* * * * *